United States Patent [19]

Todd et al.

[11] Patent Number: 4,632,114
[45] Date of Patent: Dec. 30, 1986

[54] URETHRAL SPHINCTER CUFF

[75] Inventors: Donald A. Todd, White House Station, N.J.; Robert E. Fischell, Silver Spring, Md.

[73] Assignees: C. R. Bard, Inc., Murray Hill, N.J.; The Johns Hopkins University, Baltimore, Md. ; a part interest

[21] Appl. No.: 715,157

[22] Filed: Mar. 22, 1985

[51] Int. Cl.$^4$ ............................................. A61B 17/00
[52] U.S. Cl. ........................... 128/346; 128/DIG. 25; 623/14
[58] Field of Search ............... 128/DIG. 25, 327, 344, 128/346, 1 R, 325; 623/14

[56] References Cited

U.S. PATENT DOCUMENTS

| | | | |
|---|---|---|---|
| 1,679,978 | 8/1928 | Konwiser et al. | 128/327 |
| 2,455,859 | 12/1948 | Foley | 128/DIG. 25 X |
| 2,756,753 | 7/1956 | Means | 128/DIG. 25 X |
| 3,628,536 | 12/1971 | Glesne | 128/327 |
| 3,730,186 | 5/1973 | Edmunds et al. | 128/DIG. 25 X |
| 4,177,815 | 12/1979 | Patel | 128/344 X |

*Primary Examiner*—Michael H. Thaler

*Attorney, Agent, or Firm*—Kane, Dalsimer, Kane, Sullivan and Kurucz

[57] ABSTRACT

A urethral sphincter cuff is adapted to be surgically implanted so as to encircle the urethra. When the sphincter cuff is filled, the urethra is squeezed, and the patient is continent. When the cuff is deflated pressure is released from the urethra and urine may flow therethrough.

The sphincter cuff is provided with a tongue and buckle to allow adjustment during surgical implantation. The tongue, on one side of the cuff, contains apertures which are adapted to fit onto studs on the buckle part. After placement and adjustment of the cuff an adhesive can be applied to secure the tongue to the buckle.

The cuff also contains an occluding diaphragm which, when filled, squeezes the urethra to inhibit fluid flow, and when unfilled remains in a second position in which no tension is applied to the urethra. Even when the diaphragm area is reduced to its minimum value (with pressure on the urethra) the diaphragm remains under tension so that its smooth surface does not wrinkle. Providing a smooth diaphragm surface pushed against the urethra reduces the possibility of local necrosis of the urethral tissue.

5 Claims, 6 Drawing Figures

U.S. Patent   Dec. 30, 1986   4,632,114
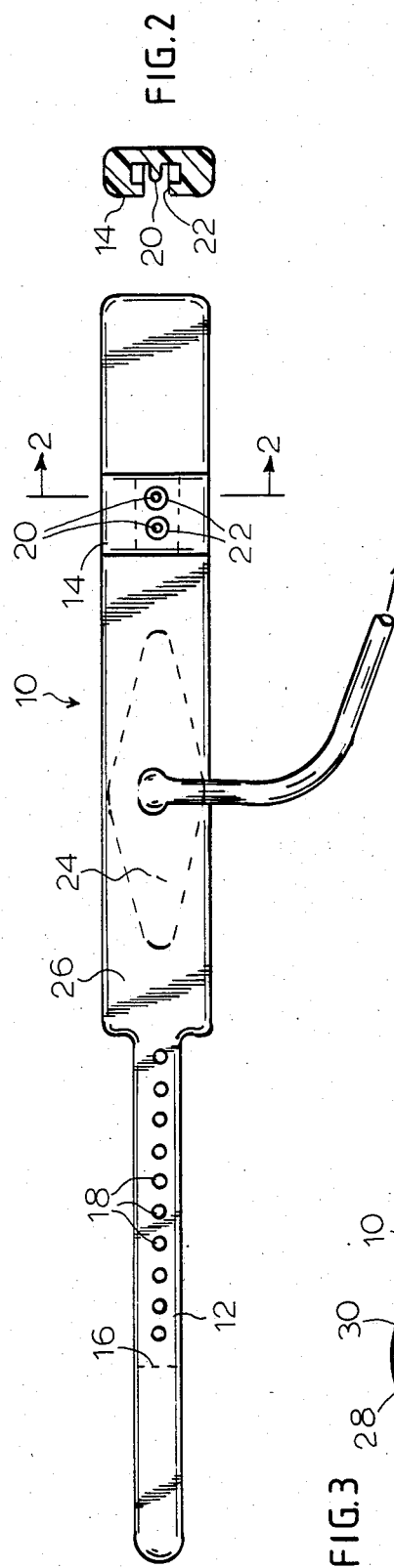
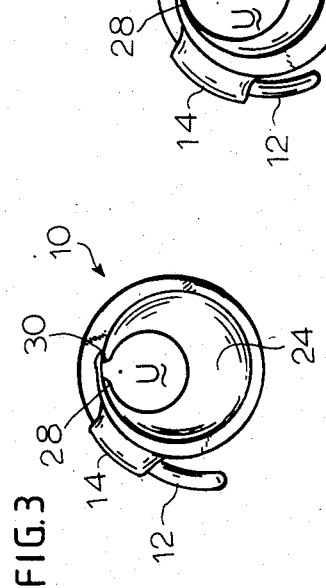
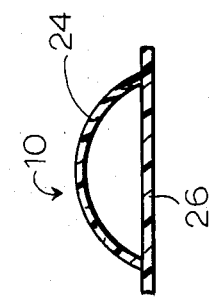
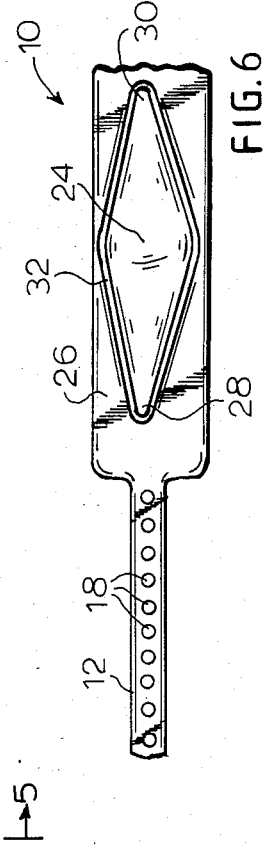

URETHRAL SPHINCTER CUFF

BACKGROUND OF THE INVENTION

Heretofore, sphincter cuffs have been made in a variety of fixed sizes from 4.5 cm in length to 11 cm in length. From 4.5 cm to 7 cm the cuffs come in 0.5 cm size gradations and from 8 cm to 11 cm they come in 1.0 cm size gradations. Thus, six sizes are required from 4.5 cm to 7 cm and four additional sizes from 8 cm to 11 cm; a total of ten different size cuffs. Obviously, a relatively large inventory of these various sizes was necessary to meet all contingencies. There was also the attendant problem of increased manufacturing and inventory costs and potential danger of utilizing or perhaps settling on a size that was not correctly fitted.

Furthermore, a major complaint from artificial sphincter implant patients is the erosion of the urethra at high pressure points. A cuff commercially being sold today consists of four separate "pillows" connected together. The areas between the pillows are open with no closing pressure necessitating the center of the pillow to compensate with extra pressure.

SUMMARY OF THE INVENTION

It is an object of the present invention to have only two cuff sizes, one small and one large, each of which is adjustable in steps of 0.25 to 0.5 cm. This has three advantages, namely:

1. There are decreased manufacturing and inventory costs if fewer sizes are made.
2. The cuff can more accurately be fitted around urethras of various diameters, and,
3. The need for changing from one size to another during the surgical procedure if one size is not quite correct when placed around the urethra is eliminated.

Another object is to pre-stretch the cuff membrane so that even in its voiding position, the diaphragm surface is still under tension.

These and other advantages of the invention are most effectively attained by a urethral sphincter cuff that is adapted to be surgically implanted so as to encircle the urethra. When the sphincter cuff is filled the urethra is squeezed, and the patient is continent. When the cuff is deflated pressure is released from the urethra and fluid may flow therethrough.

The sphincter cuff is provided with a tongue and buckle to allow adjustment during surgical implantation. The tongue, on one side of the cuff, contains apertures which are adapted to fit onto studs on the buckle part. After placement and adjustment of the cuff an adhesive can be applied to secure the tongue to the buckle.

The cuff also contains an occluding diaphragm which, when filled, squeezes the urethra to inhibit fluid flow, and when unfilled remains in a second position in which no pressure is applied to the urethra. Even when the diaphragm circumference is reduced to its minimum value (with pressure on the urethra) the diaphragm remains under tension so that its surface does not wrinkle. Providing a smooth diaphragm surface pushed against the urethra reduces the possibility of local necrosis of the urethral tissue.

Other objects and advantages of this invention will become apparent from the following detailed description which is to be taken in conjunction with the accompanying drawings.

BRIEF DESCRIPTION OF THE DRAWINGS

In the drawings:

FIG. 1 is a plan view of an extended adjustable diameter sphincter cuff of the present invention.

FIG. 2 is a cross-sectional view taken along the line 2—2 of FIG. 1.

FIG. 3 is an end view showing the cuff in its closed (continent) position.

FIG. 4 is a similar view showing the cuff in its open (voiding) position.

FIG. 5 is a sectional view taken along the line 5—5 of FIG. 4.

FIG. 6 is a fragmentary plan view of the opposite side of the cuff of FIG. 1 showing the preferred shape and construction of the diaphragm.

DETAILED DESCRIPTION OF THE DRAWINGS

In the drawings, a silicone rubber sphincter cuff 10 is illustrated that is adjustable in size after it has been placed around the urethra U. In FIG. 1 is shown the sphincter cuff 10 when fully extended. A long tongue 12 is provided for the convenience of the surgeon in order to facilitate the placement of the cuff 10 around the urethra during surgical implant. A buckle 14 is provided on the cuff 10 into which the tongue 12 is slipped and pulled through, thereby tightening the cuff so as to encircle the urethra forming a closed cylinder as shown in FIGS. 3 and 4. As seen in these figures, excess tongue is cut off as for example along line 16, after the cuff encloses the urethra.

The tongue 12 has holes 18 to which fit two sprockets 20 in the buckle. Thus, after assembly, the sprockets hold the tongue 12 in place. To further assure that the tongue 12 will not release after surgical implantation of the cuff 10, holes 22 are provided in the outer surface of the buckle 14 over the sprockets 20 so that Type A, Medical Grade Silicone Adhesive, for example, can be applied to secure the tongue 12 to the buckle 14.

A substantially oval shaped diaphragm 24 is attached at its edges to the main body 26 of the cuff 10 with silicone adhesive. Prior to and during its attachment to the main cuff body 26, the diaphragm is extensively stretched in a manner explained in detail below. Thus, the diaphragm surface is under tension at all times.

Another important aspect of the present invention is the relatively smooth transition at points 28 and 30 in FIG. 4. Ideally as the cuff 10 is inflated, the opening defined by the diaphragm 24 should always remain a perfect circle with the center shifting in the C direction as viewed in FIG. 4 when the cuff is filled. The cuff diaphragm 24 depicted in detail in FIG. 6 produces this desirable result. A bond line 32 shows where the body 26 is glued to the diaphragm 24. It has been determined that the smooth transition at 28 and 30 is achieved by tapering the ends down to a small turning radius.

The cuff is made by bonding the body 26 which is preferably relatively stiff and may be silicone and the diaphragm 24 which is preferably soft and possessing high elongation along bond line 32. The desired tensions are built into the diaphragm by first molding into a circular shape. The molded part in accordance with a preferred embodiment is approximately 2" in diameter. Tension is applied by stretching over approximately a 4" ring. In the stretched condition, the diaphragm 24 is bonded to the stiff backing. The cuff is finished off by trimming off the excess diaphragm outside the bond line. After some additional finishing, the cuff 10 is ready for use.

Two positions of the diaphragm 24 are shown in FIGS. 3 and 4. The first position noted in FIG. 3 is when the sphincter cuff 10 is full. In this position, the urethra U is squeezed and the patient should be continent. At this position, the circumference of the diaphragm 24 is at its maximum length. However, because the diaphragm was attached to the cuff body 26 under great tension, even when the diaphragm circumference is reduced to its minimum value, it still remains under some (decreased) tension so that its surface does not wrinkle. Providing a smooth diaphragm surface pushed against the urethra reduces the possibility of local necrosis of the urethral tissue. This feature is a distinct improvement over the sphincter cuff of the commercially available prior art which does not have a smooth surface when expanded with fluid and thus can pinch the urethral tissue causing local necrosis.

When fluid is removed from the sphincter cuff 10 to allow voiding (as shown in FIG. 4), the circumference of the diaphragm 24 is decreased. In this position, the diaphragm 24 is still under tension and, therefore, it retains its smooth surface. Thus, with the present invention, the sphincter cuff 10 retains its smooth surface at all times.

Thus, the foregoing disclosed sphincter cuff offers the following advantages and attributes by providing:
1. An inflatable urethral sphicter cuff that is in the form of a belt whose closed length is adaptable to various diameters of the human urethra.
2. A tongue and buckle sprocket means for assuring that the sphincter cuff retains its closed, encircling characteristics for an indefinitely long time after implant.
3. A method of applying silicone adhesive through a hole in a buckle and onto a tongue hole and sprocket to further assure that the sphincter cuff retains its closed, urethral encircling characteristic for an indefinitely long time after implantation.
4. A tongue with extra length capable of being shortened that facilitates the implantation of the sphincter cuff around the urethra.
5. A sphincter cuff diaphragm that is maintained in tension at its maximum and minimum area so that local urethral pinching during the continent maintaining state is prevented.

Thus, the several aforenoted objects and advantages are most effectively attained. Although several somewhat preferred embodiments have been disclosed and described herein, it should be understood that this invention is in no sense limited thereby and envisions other medical applications as well where it may be desired to either restrict or start/stop fluid flow in a body vessel. Accordingly, the scope of this invention is to be determined by that of the appended claims.

What is claimed is:

1. An inflatable urethral sphicter cuff adapted for application to a human urethra comprising in combination:

a belt having an inner face;

an occluding diaphragm mounted on the inner face of the belt and when in a substantially planar state being pre-stretched in substantially all lateral directions within the plane to always be under tension when in use so that it is free of wrinkles when the diaphragm is inflated and deflated whereby when the diaphragm circumference is reduced to its minimum value, with pressure on the urethra, the diaphragm remains under tension so that its surface is free of wrinkles, thereby providing a smooth diaphragm surface pushed against the urethra to reduce the possibility of local necrosis of the urethral tissue;

a coupling means for cooperating with a pressure source for selectively inflating and deflating the diaphragm;

whereby when the diaphragm is inflated the urethra will be squeezed and the patient is continent, and when the diaphragm is deflated the urethra is released and urine may flow therethrough.

2. The invention in accordance with claim 1 wherein the belt includes a tongue at one end and buckle at the other end, adjustment means provided by cooperating surfaces of the tongue and buckle for adapting the sphincter cuff to various diameters of the human urethra.

3. The invention in accordance with claim 2 wherein the adjustment means includes a series of aligned holes in the tongue and at least one sprocket in the buckle for reception by at least one of the holes.

4. The invention in accordance with claim 3 wherein securing means secures the tongue to the buckle after adjustment of the cuff.

5. The invention in accordance with claim 4 wherein the buckle includes adhesive reception means cooperating in defining the securing means which further includes an adhesive in the reception means for anchoring the sprocket in the selected hole for assuring the sphincter cuff remains closed.

* * * * *